US010555699B2

(12) United States Patent
Dellimore et al.

(10) Patent No.: US 10,555,699 B2
(45) Date of Patent: Feb. 11, 2020

(54) METHOD AND DEVICE FOR THE NON-INVASIVE MONTIORING AND IDENTIFICATION OF DRUG EFFECTS AND INTERACTIONS

(71) Applicant: KONINKLIJKE PHILIPS N.V., Eindhoven (NL)

(72) Inventors: Kiran Hamilton J. Dellimore, Utrecht (NL); Murtaza Bulut, Eindhoven (NL); Ronaldus Maria Aarts, Geldrop (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 608 days.

(21) Appl. No.: 15/124,064

(22) PCT Filed: Mar. 18, 2015

(86) PCT No.: PCT/EP2015/055602
§ 371 (c)(1),
(2) Date: Sep. 7, 2016

(87) PCT Pub. No.: WO2015/150069
PCT Pub. Date: Oct. 8, 2015

(65) Prior Publication Data
US 2017/0027505 A1 Feb. 2, 2017

(30) Foreign Application Priority Data
Mar. 31, 2014 (EP) .................................. 14162834

(51) Int. Cl.
*A61M 5/48* (2006.01)
*A61B 5/00* (2006.01)
(Continued)

(52) U.S. Cl.
CPC .......... *A61B 5/4848* (2013.01); *A61B 5/0022* (2013.01); *A61B 5/4833* (2013.01);
(Continued)

(58) Field of Classification Search
CPC ...... G06F 19/00; G06F 19/324; G06F 19/326; G06F 19/34; G06F 19/3456;
(Continued)

(56) References Cited

U.S. PATENT DOCUMENTS

| 2002/0095313 A1 | 7/2002 | Haq |
| 2003/0106553 A1 | 6/2003 | Vanderveen |

(Continued)

FOREIGN PATENT DOCUMENTS

| CA | 2451992 C | 11/2002 |
| CN | 102737165 A | 10/2012 |

(Continued)

OTHER PUBLICATIONS

Ozdalga et al., The Smartphone in Medicine: A Review of Current and Potential Use Among Physicians and Students, Journal of Medical Internet Research, 14(5) (Year: 2012).*

(Continued)

*Primary Examiner* — Bhisma Mehta
*Assistant Examiner* — Hong-Van N Trinh

(57) ABSTRACT

A method for use in detecting and monitoring effects experienced by a subject taking a first drug, drug A, and at least one other substance, substance B, the method comprising: (a) obtaining a plurality of measured values of a physiological characteristic of the subject over a time period; (b) comparing the measured values to a predefined signature, the drug A signature, associated with the first drug, and thereby calculating a measure, $A_{diff}$, of the difference between the measured values and the drug A signature; (c) comparing the measured values to a predefined signature, the substance B signature, associated with the at least one other substance, and thereby calculating a measure, $B_{diff}$, of the difference between the measured values and the substance B signature; (d) comparing the measured values to a (Continued)

predefined signature, the DO signature, associated with a desired physiological state of the subject, and thereby calculating a measure, $DO_{diff}$, of the difference between the measured values and the DO signature; and (e) combining $A_{diff}$ and $DO_{diff}$ to produce an output.

10 Claims, 4 Drawing Sheets

(51) Int. Cl.
*G06F 19/00* (2018.01)
*A61J 7/00* (2006.01)

(52) U.S. Cl.
CPC .......... *A61B 5/4839* (2013.01); *A61B 5/6898* (2013.01); *A61B 5/746* (2013.01); *A61J 7/0076* (2013.01); *G06F 19/3456* (2013.01)

(58) Field of Classification Search
CPC ............. G06F 19/3462; G06F 19/3468; G06F 19/3475; G01N 2800/52; G16H 15/00; G16H 50/00; G16H 50/20; A61B 5/0022; A61B 5/4833; A61B 5/4836; A61B 5/4839; A61B 5/4848; A61B 5/0002; A61B 5/0004; A61B 5/0006; A61B 5/0008; A61B 5/0011; A61B 5/0015; A61B 5/002; A61B 5/0024; A61B 5/411; A61B 5/14532; A61M 2230/005; A61M 2230/04; A61M 2230/30; A61M 2230/40; A61M 2230/50
See application file for complete search history.

(56) References Cited

U.S. PATENT DOCUMENTS

| | | |
|---|---|---|
| 2005/0177397 A1 | 8/2005 | Kane |
| 2006/0089592 A1* | 4/2006 | Kadhiresan .......... A61M 5/142 604/65 |
| 2007/0156893 A1 | 7/2007 | Brown |
| 2008/0234322 A1* | 9/2008 | Syroid .................. A61K 31/02 514/326 |
| 2008/0234992 A1 | 9/2008 | Ray et al. |
| 2010/0280329 A1 | 11/2010 | Randlov et al. |
| 2011/0004110 A1 | 1/2011 | Shusterman |
| 2013/0179184 A1 | 7/2013 | Hurst |
| 2014/0055589 A1 | 2/2014 | Bangera et al. |

FOREIGN PATENT DOCUMENTS

| | | |
|---|---|---|
| EP | 1363225 A2 | 11/2003 |
| EP | 1419730 A1 | 5/2004 |
| EP | 1522257 A1 | 4/2005 |
| WO | 9720496 A1 | 6/1997 |
| WO | 2004036182 A2 | 4/2004 |
| WO | 2011112972 A2 | 9/2011 |

OTHER PUBLICATIONS

Verkruysse et al, "Remote Plethysmographic Imaging Using Ambient Light", Optics Extress, vol. 16, No. 26, 2008, pp. 21434-21445.
Wieringa et al, "Contactless Multiple Wavelength Photoplethysmographic Imaging: A First Step Toward "SpO2 Camera" Technology", Annals of Biomedical Engineering, vol. 33, No. 8, 2005, pp. 1034-1041.
Blood Pressure Chart, Vaughn's Summaries, Downloaded From http://www.vaughns-1-pagers.com/medicine/blood-pressure.htm on Sep. 7, 2016, 15 Pages.

* cited by examiner

METHOD AND DEVICE FOR THE NON-INVASIVE MONTIORING AND IDENTIFICATION OF DRUG EFFECTS AND INTERACTIONS

CROSS-REFERENCE TO PRIOR APPLICATIONS

This application is the U.S. National Phase application under 35 U.S.C. § 371 of International Application No. PCT/EP2015/055602, filed on Mar. 18, 2015, which claims the benefit of European Patent Application No. 14162834.7, filed on Mar. 31, 2014. These applications are hereby incorporated by reference herein.

TECHNICAL FIELD OF THE INVENTION

The invention relates to a method and device for use in monitoring and identifying drug effects and interactions. More particularly, the invention relates to a method and device for the non-invasive monitoring and identification of the effects of a drug on a subject taking that drug.

BACKGROUND TO THE INVENTION

Prescription drug therapy is widely used to treat various medical conditions and disorders. Many prescription drugs produce side effects and adverse reactions in subjects, which can lead to considerable discomfort and poor quality of life. Also, many prescription drugs interact with other drugs and/or with foods such that they do not work as intended when taken alongside these other drugs/foods. Drug-drug and/or drug-food interactions can mean that prescription drugs with a narrow therapeutic window (such as warfarin, lidocaine, digoxin, lithium, phenytoin, etc.) may become toxic, producing many severe side effects and strong adverse reactions even at low dosing levels.

A system for mitigating this issue for use by medical professionals is described in US 2002/0095313. The US '313 system requires all prescriptions and drug orders to be generated using a computer having a built-in error correction system. The error-correction system has access to data on which drugs have already been prescribed for a given subject and/or foods the subject eats, as well as a database containing information on drug-drug interactions and drug-food interactions. When a new drug is prescribed for the subject, the system uses the database to check for interactions between the new drugs and the already prescribed drugs and/or the foods the subject eats and produces an alarm if an interaction is found.

An alternative system, for use by subjects, is described in EP 1363225. The EP '225 system provides a user with a barcoded subscriber card, where the barcode uniquely identifies the user, and a device having a barcode reader. The user scans the barcode of a product (e.g. a food product or an over-the-counter medication) and their subscriber card, and the device communicates the barcode information to an application that looks up (e.g. by using an internet connection to access one or more central databases) the user's profile (which contains information about the user's prescriptions, allergies, chronic illnesses and/or other user specific information product ingredients) and the ingredients of the product. The application compares the ingredients to the user's profile and the results of the comparison are sent back to the user.

Both of these systems suffer from the drawback that the food and drug interactions which may be experienced by a given subject are identified solely based on a database of known drug and food interactions. They cannot detect interactions which are not documented in the databases, and they cannot detect or monitor side effects and/or adverse reactions which the subject actually experiences. However; the huge variety of different prescription drugs, over-the-counter drugs and foods which are available means that many, if not most, of the possible combinations of a given drug with another drug or food have not been tested for adverse reactions. Furthermore, it may often be the case that a drug is taken alongside more than one other drug and/or food that could interact with it. In such situations the interaction is unlikely to have been documented, and the resulting effects can be difficult to predict from first principles.

It is therefore desirable to be able to detect the side effects and adverse reactions due to drug-drug and/or drug-food interactions which are actually experienced by a subject taking a given drug. By knowing the actual side effects and adverse reactions experienced by a subject, one can take measures to relieve them, for example by varying the drug dose prescribed. In this way, the health and quality of life of a subject can be improved considerably. Furthermore, it is desirable to detect such side effects and adverse reactions at an early stage so that a severe adverse reaction can be avoided.

Examples of circumstances in which a subject, caregiver or physician may want to be able to detect and/or monitor the side effects and adverse reactions that are experienced by a subject taking a particular drug include:
- if the subject wants to lead an active and normal daily life but is unable to do so because of the discomfort or malaise caused by severe side effects and adverse reactions;
- if the caregiver or physician wants to determine whether the drug dose needs to be altered during treatment for a particular medical condition to improve therapeutic effectiveness or prevent toxicity;
- if the subject wants to begin taking a particular new drug or food alongside their existing drug therapy;
- if the physician or caregiver wants to closely manage the therapy of a high risk subject, e.g., one who has liver or kidney failure;
- if the physician wants to determine the best drug dose for a specific subject to minimizes side effects and adverse reactions;
- to find out whether there has been an error in the drug dose prescribed;
- to determine the best time for administering a drug;
- if the physician wants to closely control the administration of a drug with a narrow therapeutic window which may become toxic even at low dosing levels.

There is therefore a need for an improved method and device that can provide a reliable determination of whether a given subject is experiencing a side effect or adverse reaction to a drug they are taking. Such a method and device could be used in a home or hospital-based monitoring system to detect the occurrence of side effects and adverse reactions, as well as for monitoring the progression of such side effects and adverse reactions as a result of adjusting the drug therapy.

SUMMARY OF THE INVENTION

A given prescription drug will typically influence the human body in several different ways, therefore its use can cause changes in a variety of physiological characteristics such as heart rate, blood pressure, heart rhythm, breathing rate, core body temperature, hydration state, movement, posture, speech quality, body weight, vision, hearing level, urine output, as well as changes in eye and skin appearance. The present invention detects physiological changes in subjects undergoing drug therapy and links them to side effects of the drug being administered, and/or adverse reactions due to drug-drug or drug-food interactions. The occurrence of side effects or adverse reactions to a given drug can therefore be detected and monitored by measuring physiological characteristics of the subject taking the drug. This enables the subject, care giver and/or physician to be warned of the occurrence of potentially severe or life threatening side effects or adverse reactions, as well as of the existence of drug-drug and/or drug-food interactions which may not have been previously documented.

According to a first aspect of the invention, there is provided a method for use in detecting and monitoring effects experienced by a subject taking a first drug, drug A, and at least one other substance, substance B, the method comprising:

(a) obtaining a plurality of measured values of a physiological characteristic of the subject over a time period;

(b) comparing the measured values to a predefined signature, the drug A signature, associated with the first drug, and thereby calculating a measure, $A_{diff}$, of the difference between the measured values and the drug A signature;

(c) comparing the measured values to a predefined signature, the substance B signature, associated with the at least one other substance, and thereby calculating a measure, $B_{diff}$, of the difference between the measured values and the substance B signature;

(d) comparing the measured values to a predefined signature, the DO signature, associated with a desired physiological state of the subject, and thereby calculating a measure, $DO_{diff}$, of the difference between the measured values and the DO signature; and (e) combining $A_{diff}$ and $B_{diff}$ and $DO_{diff}$ to produce an output.

There is also provided, according to a second aspect of the invention, a device for use in detecting and monitoring effects experienced by a subject taking a first drug, drug A, and at least one other substance, substance B, the device comprising:

a memory configured to store a first predefined signature, the drug A signature, associated with the first drug, a second predefined signature, the substance B signature, associated with the at least one other substance, and a third predefined signature, the DO signature, associated with a desired physiological state of the subject; and a control unit in communication with the memory, wherein the control unit is arranged to:

(i) receive from a sensor measured values of one or more physiological characteristics of a subject;

(ii) compare the received measured values to the drug A signature and thereby to calculate a measure, $A_{diff}$, of the difference between the measured values and the drug A signature;

(iii) compare the measured values to the substance B signature and thereby calculate a measure, $B_{diff}$, of the difference between the measured values and the substance B signature;

(iv) compare the measured values to the DO signature and thereby calculate a measure, $DO_{diff}$, of the difference between the measured values and the DO signature;

(v) combine $A_{diff}$ and $B_{diff}$ and $DO_{diff}$ to produce an output.

The device may be detachably coupleable to the sensor or the sensor may be included in the device.

There is also provided, according to a fourth aspect of the invention, a drug administration system comprising the device of the second aspect of the invention. In an embodiment the drug administration system includes a pill dispenser or an infusion pump.

There is also provided, according to a fifth aspect of the invention, a medical instrument or system for detecting a physiological parameter of a subject and controlling an alarm. The medical instrument or system comprises the device of the second aspect of the invention. The medical instrument or system may be a bed side monitor monitoring a vital sign of a patient in a hospital.

There is also provided, according to a sixth aspect of the invention, a smartphone comprising the device of the second aspect of the invention. A camera included in the smartphone is used to monitor a vital sign of a subject. The display on the smartphone may provide message to the subject comprising information indicating that an adverse reaction is being experienced.

There is also provided, according to a seventh aspect of the invention, a computer program product, comprising computer readable code, the computer readable code being configured such that, on execution by a suitable computer or processor, the computer or processor performs the method according to the first aspect of the invention. The computer program product may be downloadable from a communication network and/or stored in a computer readable and/or microprocessor-executable medium.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE PREFERRED EMBODIMENTS

Figure 1:
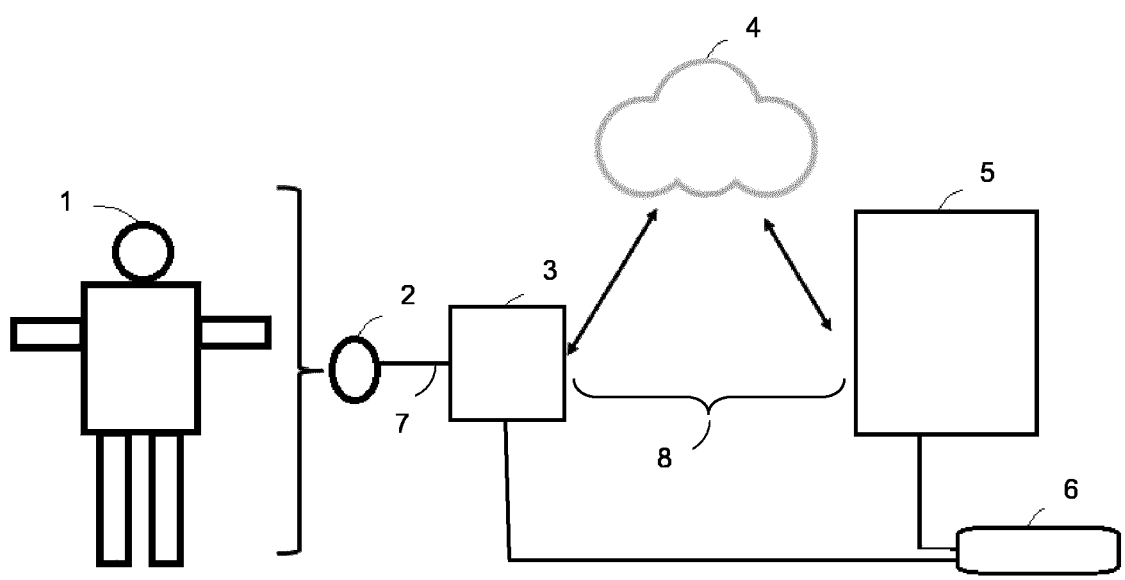
FIG. 1 is an illustration of a device for monitoring and identifying drug-related effects according to an embodiment.

FIG. 1 shows a device for use in monitoring and identifying drug-related effects according to an embodiment of the invention. The device is detachably coupled to at least one sensor 2 for measuring one or more physiological characteristics of a subject 1. The device may be wireless coupled to the sensor. Preferably the at least one sensor 2 is non-invasive, and is arranged to take measurements at least semi-continuously. The one or more measured physiological characteristics may include, for example, heart rate, blood pressure, heart rhythm, breathing rate, core body temperature, movement, speech quality, eye appearance, skin appearance, body weight, posture, hydration state, vision, hearing level, urine level, etc. In some embodiments the device is coupled to a variety of different sensors 2 so that several different physical or physiological characteristics can be measured. The sensors may be integrated into another device or may be included in the device.

The sensor 2 may be any device which is capable of measuring a physical or physiological characteristic of the subject. The sensor 2 may comprise, for example, an accelerometer, a GPS receiver, a thermometer, a blood pressure monitor, a ventilator, or an ECG, EEG or other electrical sensor. Using the at least one sensor 2, one or more aspects of the subject's state over time can be monitored. Various systems and methods for obtaining measurements of many different physiological and physical characteristics, including those listed above, are known in the art.

The device includes a control unit 3 connected to the at least one sensor 2 by communications link 7. In some embodiments the control unit is also connected by a communications link 8 to a remote server 5. The communications link 7 between the control unit 3 and the at least one sensor 2 is preferably wireless, utilizing a protocol such as Wi-Fi, Bluetooth or ZigBee. It will be appreciated, however, that any form of wired or wireless connection which allows data to be communicated between the control unit 3 and a sensor may be used. Furthermore, where several sensors are present, the communications links to each of the sensors need not all be of the same type. The same applies to the communications link 8 between the control unit 3 and the remote server 5, if present. In the illustrated embodiment, the communications link 8 communicates data between the control unit 3 and the remote server 5 via the internet 4.

In some embodiments the device further includes a display and a speaker (not shown) for presenting information to a user, e.g. a warning that the subject may be experiencing an adverse reaction to a drug. In some such embodiments the display and/or speaker are integrated into the same device as the control unit 3.

Recently, non-contact, remote PPG (rPPG) devices (also called camera rPPG device herein) for unobtrusive measurements have been introduced. Remote PPG utilizes light sources or, in general radiation sources, disposed remotely from the subject of interest. Similarly, also a detector, e.g., a camera or a photo detector, can be disposed remotely from the subject of interest. Therefore, remote photoplethysmographic systems and devices are considered unobtrusive and well suited for medical as well as non-medical everyday applications.

Verkruysse et al., "Remote plethysmographic imaging using ambient light", Optics Express, 16(26), 22 Dec. 2008, pp. 21434-21445 demonstrates that photoplethysmographic signals can be measured remotely using ambient light and a conventional consumer level video camera, using red, green and blue colour channels.

Wieringa, et al., "Contactless Multiple Wavelength Photoplethysmographic Imaging: A First Step Toward "SpO2 Camera" Technology," Ann. Biomed. Eng. 33, 1034-1041 (2005), discloses a remote PPG system for contactless imaging of arterial oxygen saturation in tissue based upon the measurement of plethysmographic signals at different wavelengths. The system comprises a monochrome CMOS-camera and a light source with LEDs of three different wavelengths. The camera sequentially acquires three movies of the subject at the three different wavelengths. The pulse rate can be determined from a movie at a single wavelength, whereas at least two movies at different wavelengths are required for determining the oxygen saturation. The measurements are performed in a darkroom, using only one wavelength at a time.

In an embodiment the device is included in a smartphone. The sensor may for example comprise an RGB camera which is integrated into the smartphone. With the camera, using PPG technology, vital signs can be measured, which are revealed by minute light absorption changes in the skin caused by the pulsating blood volume, i.e. by periodic color changes of the human skin induced by the blood volume pulse. Vital signs of a person, for example the heart rate (HR), the respiration rate (RR) or the arterial blood oxygen saturation, serve as indicators of the current state of a person and as powerful predictors of serious medical events. For this reason, vital signs are extensively monitored in inpatient and outpatient care settings, at home or in further health, leisure and fitness settings.

In a further embodiment the device is included in a medical instrument or system for detecting a physiological parameter of a subject and controlling an alarm, the alarm being in dependence of the output provided by the device. The medical instrument or system may be a bed side monitor or patient monitor for monitoring a vital sign of a patient in a hospital. Typical patient monitoring systems measure different physiological values, and may provide measurements of ECG, respiration, SpO2, blood pressure etc. If in the medical instrument or system for detecting a physiological parameter according to the invention a detected physiological parameter exceeds or under-runs a preset limit due to a side effects and/or adverse reaction to a drug administered to the patient an alarm is generated.

In some embodiments the device is (wired or wirelessly) connectable to an automated drug administration system (for example a pill dispenser or an infusion pump, not shown), such that a control signal that is dependent on the output provided by the device can be used to directly control one or more parameters relating to the administration of a drug and/or substance.

The control unit 3 comprises a communications interface, a memory, and a processing unit (not shown). The communications interface is configured to establish the communications links 7 with the at least one sensor 2. Preferably the communications link 7 enables the control unit 3 to engage in two-way communication with the at least one sensor 2, so that the control unit may receive data from the sensor and also transmit control information to the sensor. In embodiments in which the control unit 3 is connected to a remote server 5 the communications interface is also configured to establish the communications link 8 with the remote server, for example using a telecommunications network. Preferably the communications link 8 enables the control unit 3 to engage in two-way communication with the remote server 5. In some embodiments the control unit 3 is configured to transmit, via the communications interface, messages to a remote device 6 (such as, for example, a mobile phone, pager, computer or fax machine), e.g. a device being used by a healthcare professional. The message may be, for example, an SMS, fax or e-mail message. In some embodiments where the control unit is connected to a remote server, the remote server 5 may additionally or alternatively be configured to transmit messages to the remote device 6.

The memory included in the device is configured to store data. At least one database containing physiological signatures for various health states is stored on the memory. In some alternative embodiments the at least one database is stored on a memory of a remote server (for example the remote server 5) and is accessible by the control unit 3. The at least one database contains at least one drug-related physiological signature (i.e. a signature associated with a particular drug). Preferably the database contains a plurality of drug-related physiological signatures, each associated with a different drug. A drug-related physiological signature is a representation of the effect that the drug is expected to have on a subject's physiology. The database also contains at least one food-related physiological signature (i.e. a signature associated with a particular food). Preferably the database contains a plurality of food-related physiological signatures, each associated with a different food. A food-related physiological signature is a representation of the effect that the food is expected to have on a subject's physiology. One or more of the drug-related or food-related signatures may be subject-specific.

In some embodiments the at least one database additionally includes at least one drug-drug interaction related physiological signature and/or at least one drug-food interaction related physiological signature. A drug-drug interaction related signature is a representation of the effect that two drugs taken together are expected to have on a subject's physiology. Likewise, a drug-food interaction related physiological signature is a representation of the physiological effect of a drug and a food taken together. Preferably the database contains a plurality of drug-drug interaction signatures and a plurality of drug-food interaction signatures.

A desired outcome physiological signature is also stored on the memory of the control unit 3, or alternatively on the memory of a remote server which is accessible by the control unit 3. This signature is a representation of the expected physiological state of the subject following successful treatment with one or more drugs. In many cases the desired outcome of the treatment is a completely healthy subject, and in such cases the desired outcome physiological signature comprises normal values for all physiological characteristics. However, that need not always be the case. For example, for subjects that need step-by-step treatment, the desired outcome of a given drug treatment may be to cure or improve one particular health condition out of several health conditions which the subject is suffering from. In these cases the desired outcome physiological signature may comprise abnormal values for physiological characteristics affected by the other health conditions. It will be appreciated that several different desired outcome signatures can be defined for different stages of a step-by-step treatment regime. Furthermore, a desired outcome signature can be updated during the course of a treatment to reflect changes in the subject's underlying health conditions. Preferably the desired outcome signature is subject-specific (i.e. it takes into account particular features of the subject in question). It will be appreciated that when the desired outcome signature is at least partly based on the subject's underlying health conditions it will necessarily be subject-specific.

Each of the physiological signatures is defined based on measurable physiological characteristics. For example, anti-hypertensive medications such as amlodipine besylate (Norvasc) and metoprolol tartrate (Lopressor) typically cause a change in a subject's blood pressure. The drug-related physiological signatures for these drugs will therefore include blood pressure values which are known to be typical for people taking the drug. If a drug is known to affect a variety of different physiological characteristics, then the drug-related signature for that drug will preferably include typical (drug-affected) values for each of the affected physiological characteristics.

In some embodiments one or more of the signatures may take the form of time-series representations of affected physiological characteristics. In some embodiments one or more of the signatures comprises a signal. In some embodiments one or more of the signatures comprises features calculated from a signal. For example, various heart rate parameters can be calculated from an ECG signal. A signal can be, for example, the output of a given measuring device or can be based on the output of one or more measuring devices. Such signals can be represented in the time-domain, the frequency-domain, or both. Such signals can be continuous, like an ECG signal, or discrete, like a blood pressure measurement.

In some embodiments, one or more of the signatures may comprise a statistical model (such as a Gaussian Mixture Model, Neural Network, Hidden Markov Model, etc.) constructed based on the affected physiological characteristics. In some embodiments statistical modelling is used to generate the signatures by calculating a probability distribution of a given feature set (constructed from clinical trial data), e.g. by calculating the histogram of the data. In such embodiments the signature comprises the calculated histogram. In some embodiments a signature is generated by fitting the data to a defined distribution, such as Gaussian, Cauchy, etc. The statistical model may be generated using one or more signals, or features calculated from one or more signals.

In some embodiments one or more of the signatures are generated individually for different physical or physiological characteristics. One or more of the signatures may be generated based on a combination of multiple physical or physiological characteristics. The combination may be performed at a feature level. For example, ECG, respiration, skin conductance, and blood pressure signals can be combined by calculating, for each signal, different statistical features and then combining all of the calculated features into vectors. In some embodiments these vectors are used directly as one or more signatures. In other embodiments the vectors are used to generate signatures, for example using automatic learning methods to select a representative set of features from a larger set of features.

In some embodiments at least some of the signatures are non-subject specific. Such signatures are comprised of values which have been determined to be typical for the situation in question, based on studies of large numbers of subjects. For example, a non-subject specific drug-related signature may comprise a time-series or signal for each of several affected physiological characteristics, where each time-series or signal is calculated using measured values obtained from a large number of subjects receiving the drug under controlled conditions (e.g. a clinical trial). In some embodiments the values or signal(s) making up a non-subject specific signature may be generated by a computer model, where the model was created using data from a large number of subjects receiving the drug under controlled conditions.

In some embodiments at least some of the signatures are subject-specific. A subject specific drug-related signature can be created for a particular drug, for example, by giving the subject only the drug in question (i.e. ensuring that they are not also taking any other drugs or foods which could interact with the particular drug) under controlled conditions and recording measurements of their physiological characteristics over the course of the treatment. The recorded measurements can then be used directly to generate a time series- or signal-based signature, or can be input into a statistical model to generate a model-based signature. Alternatively, signatures generated using data obtained from a large number of subjects receiving the drug under controlled conditions (hereinafter referred to as clinical trial data) can be made subject-specific by differentially weighting the physiological characteristics or features comprised in the signature based on subject-specific factors such as the medical history, weight, age, compliance record of the subject, etc. If a patient has hypertension, for example, blood pressure features can be weighted more highly than physical characteristics unrelated to blood pressure, such as urine output. It will be appreciated that subject-specific food-related, drug-drug interaction, and/or drug-food interaction signatures can also be created.

The processing unit is linked to the memory such that it can access the data stored in the memory and can save data to the memory. The processing unit is also linked to the communications interface, such that the processing unit can transmit to and receive data from the at least one sensor 2 and, if present, the remote server 5.

The control unit 3 can implement the drug effects monitoring method that is described below and shown in FIG. 2. Alternatively, the control unit 3 can transmit data acquired by the at least one sensor 2, and or data generated by the control unit 3 on the basis of data acquired by the sensor 2, to the remote central server 5. A processing unit of the remote central server 5 may then implement some of steps in the method shown in FIG. 2.

Figure 2:
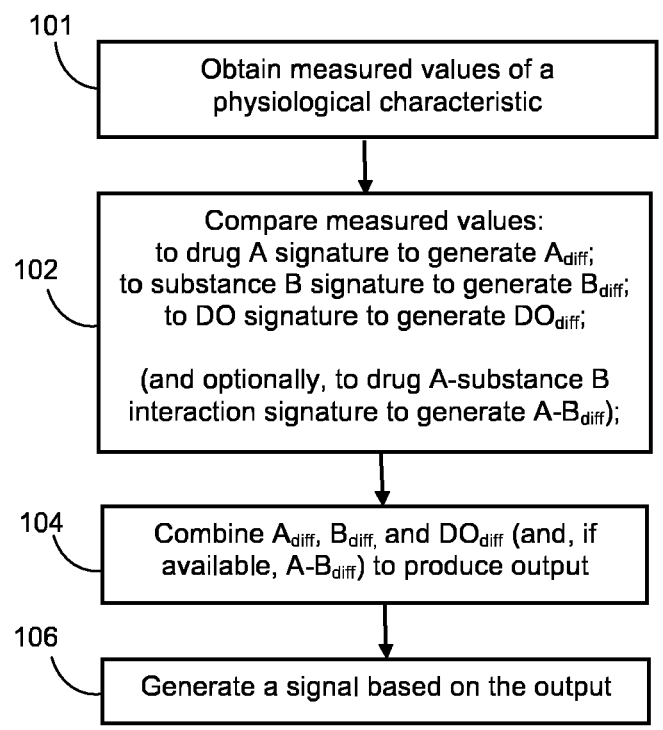
FIG. 2 is a flow chart illustrating a method for use in monitoring and identifying drug-related effects according to a general embodiment of the invention.

FIG. 2 shows a method for use in monitoring the effects of a drug (drug A) on a subject according to an embodiment of the invention. The subject is known to be taking a second substance (substance B) alongside drug A.

In step 101, a plurality of values of one or more physical or physiological characteristics of the subject are measured over a time period. In some embodiments the physiological characteristics which are measured are selected based on factors relating to the nature of drug A and/or the nature of substance B, and/or other factors specific to the subject. In preferred embodiments these measurements are carried out by the sensor 2. Preferably the measurements are performed continuously or semi-continuously over the time period. In some embodiments the time period is predefined. In some embodiments the time period is indefinite (i.e. measurements are performed continuously whilst the system is in operation. The measured values acquired by the sensor 2 are then communicated to the control unit 3. In some embodiments this communication occurs whenever a new measured value is acquired. In alternative embodiments the sensor 2 is configured to communicate the most recently acquired measured values to the control unit 3 at the expiry of the time period. In some embodiments the control unit 3 stores the received measured values in a database in its memory.

In step 102, the measured values are compared to signatures. This step comprises comparing the measured values to the drug-related signature for drug A (the drug A signature). In preferred embodiments the drug A signature comprises a time variant set of expected values for one or more physical or physiological characteristics. In such embodiments, preferably the physical or physiological characteristics for which expected values are provided include or are the same as the physiological characteristics which are measured by the sensor 2. The expected values are values of the physiological characteristics which may be expected for a subject taking drug A in isolation.

In some embodiments the comparison of the measured values with the drug A signature is performed by the control unit 3 (using its processing unit). The comparison may be performed by comparing the measured values for each physiological characteristic with the expected values for those characteristics which make up the drug A signature. Preferably the comparison involves calculating a measure of the difference ($A_{diff}$) between the measured values and the drug A signature. The difference between the measured values and the drug A signature represents the interaction between drug A and substance B (i.e. how the effects of drug A are altered by the presence of substance B). $A_{diff}$ therefore depends on the effects of substance B on the subject and on the function of drug A.

The measure $A_{diff}$ may be calculated by calculating a difference for each physiological characteristic individually and then combining these differences. Alternatively, some or all of the measured physiological characteristics may be considered together in the calculation of $A_{diff}$. In preferred embodiments, multiple features extracted from the measured values are analyzed together.

In some embodiments, e.g. embodiments where the signature is time series-based, the comparison involves determining whether (and by how much) the measured values deviate from the corresponding expected values. In some such embodiments the comparison involves determining whether the measured values deviate from the corresponding expected values by more than a predefined deviation threshold. In some such embodiments $A_{diff}$ is calculated in response to a determination that at least some of the measured values deviate from the corresponding expected values by more than the predefined deviation threshold. Preferably the threshold is defined based on factors such as the subject's medical history, the type of drug being administered, and/or the quality of the measured data. In some embodiments the threshold is dynamically updatable, so that it can be altered during operation of the system.

In some embodiments, e.g. embodiments where the signature comprises a time-domain signal, the comparison involves calculating an error signal using the energy of the difference signal. In embodiments in which a signature comprises vectors, then the difference between vectors is calculated, and the MSE (mean squared error) (or any other similarity metric) is calculated.

In embodiments in which a signature comprises a statistical model, $A_{diff}$ may be calculated by inputting the measured values to the model. In some embodiments calculating $A_{diff}$ involves applying statistical tests (e.g. simple analysis of variance (ANOVA) or analysis of covariance (ANCOVA) tests, or other more advanced statistical tests) to determine whether differences between the measured values and the signature are statistically significant. In some embodiments calculating $A_{diff}$ involves evaluating the goodness of fit of a statistical model into which the measured values have been input with the expected statistical model for one or more physiological characteristics and/or features.

In some embodiments, calculating $A_{diff}$ involves the use of automatic learning techniques (such as those commonly employed in speech recognition and related fields). For example, features calculated from clinical trial data can be used to train a classification or likelihood calculation system. The training can be done using techniques such as support vector machines, Bayesian learning, Neural networks, Hidden Markov Models, etc. Then it is determined how well the measured data fits these models.

Step 102 also comprises comparing the measured values to a signature for substance B (the substance B signature), which may be a drug-related signature (if substance B is another drug) or a food-related signature (if substance B is a food). In preferred embodiments the substance B signature comprises a time variant set of expected values for one or more physical or physiological characteristics. In such embodiments, preferably the physical or physiological characteristics for which expected values are provided include or are the same as the physiological characteristics which are measured by the sensor 2. The expected values are values of the physiological characteristics which may be expected for a subject taking substance B in isolation. Preferably the comparison of the measured values with the substance B signature is performed in the same manner as the comparison of the measured values with the drug A signature. The comparison of the measured values with the substance B signature involves calculating a measure of the difference ($B_{diff}$) between the measured values and the substance B signature. The difference between the measured values and the substance B signature represents the interaction between substance B and drug A (i.e. how the effects of substance B are altered by the presence of drug A). $B_{diff}$ therefore depends on the effects of drug A on the subject and on the function of substance B. Preferably the measure $B_{diff}$ is calculated in the same way as the measure $A_{diff}$.

Step 102 also comprises comparing the measured values to a desired outcome signature (the DO signature). In some embodiments the DO signature comprises a time variant set of expected values for one or more physical or physiological characteristics. In such embodiments, preferably the physical or physiological characteristics for which expected values are provided include or are the same as the physiological characteristics which are measured by the sensor 2. The expected values are values of the physiological characteristics which may be expected if the treatment being administered to the subject is successful. Preferably the comparison of the measured values with the DO signature is performed in the same manner as the comparison of the measured values with the drug A signature and/or the comparison of the measured values with the substance B signature. The comparison of the measured values with the DO signature involves calculating a measure of the difference ($DO_{diff}$) between the measured values and the DO signature. Preferably the measure $DO_{diff}$ is calculated in the same way as the measure $A_{diff\ and}$/or as the measure $B_{diff}$.

Optionally, step 102 also comprises comparing the measured values to a signature representing the interaction of drug A and substance B (i.e. a drug-drug interaction signature if substance B is a drug, or a drug-food interaction signature if substance B is a food), if such an interaction signature is available. The result of such a comparison will comprise, for example, a measure of the difference ($A-B_{diff}$) between the measured values and the A-B interaction signature. Preferably the measure $DO_{diff}$ is calculated in the same way as the measure $A_{diff\ and}$/or as the measure $B_{diff}$.

In some embodiments one or more of the difference measures (i.e. $A_{diff}$, $B_{diff}$, $DO_{diff}$, $A-B_{diff}$) comprises multiple difference values, for example for different physiological characteristics or features. A difference value can be calculated, for example, for an individual physiological characteristic or feature. Alternatively, a single difference value can be generated based on a combination or cluster of several physiological characteristics or features. Preferrably individual difference values are generated for the physiological characteristics or features that are most relevant, e.g., to the clinical management of the therapeutic drug treatment and/or to the subject's health condition and medical history, whilst physiological characteristics or features which are less relevant are combined or clustered.

In step 104, the difference measures $A_{diff}$, $B_{diff}$ and $DO_{diff}$ (and, if available, $A-B_{diff}$) are combined to produce an output. The combination is done in an adaptive manner, by differentially weighting each signature. In embodiments where the difference measures comprise multiple difference values, weighting the signatures can comprise differentially weighting each individual difference value comprised in a difference measure.

Weights may be assigned, for example, according to the subject state (current and historical), and/or according to the relative importance of the physiological characteristics with respect to the particular health condition that the subject is being treated for, and/or according to the quality of the data for each measured physiological characteristic, and/or according to the variability in each measured physiological characteristic. For example, if the subject has a history of hypertension, a value associated with a blood pressure feature may be assigned a greater weight than values associated with features known to be less relevant to hypertension such as speech quality, body weight, core temperature, urine output, etc. If the subject also has another comorbid condition, such as diabetes, then a value associated with blood glucose will also be assigned a relatively greater weight. As another example, if a particular physiological characteristic has been observed to show relatively high variability compared to other monitored physiological characteristics, a value associated with that physiological characteristic may be assigned a relatively greater weight. As another example, if the quality of the data for a physiological characteristic is poor, a value associated with that physiological characteristic may be assigned a relatively lesser weight. In some embodiments the weights are dynamically updated during operation of the system, for example if the data quality or variability associated with a particular physiological characteristic changes. In some such embodiments, a self-learning algorithm (such as K-means clustering, K Nearest neighbors, or any other unsupervised learning algorithm) is used to perform the updating as new information is acquired.

The weights are defined such that they add up to unity (i.e. $w1+w2+w3+w4+\ldots=1$). Depending on the number of values being combined, the number of the weights will change. In some embodiments, if no medical history information is available for the subject, and if the data quality (determined, for example, in terms of signal to noise ratio, missing values, inserted values, signal shape, signal amplitude, signal duration) for each of the measured physiological characteristics is equivalent then all weights will be equal. However, this is unlikely since medications are generally designed to achieve a specific effect (e.g. lowering the blood pressure) so some physiological characteristics will always be more relevant than others. A relatively greater weight can be assigned to a given difference value, e.g. a difference value associated with a blood pressure feature, by increasing the weight for this difference value by a certain incremental factor w1+delta, and accordingly decreasing the weights for all of the other difference values in the combination so that sum of the weights is still 1.

In some embodiments the combining comprises adding the difference measures $A_{diff}$ and $DO_{diff}$. In some such embodiments the combining comprises calculating a weighted sum of the difference measures $A_{diff}$ and $DO_{diff}$. In some embodiments the combining comprises calculating a weighted sum of individual difference values comprised in the difference measures.

The combining may involve comparing the difference measures $A_{diff}$ and $B_{diff}$ (and, if available, $A-B_{diff}$) to assess their relative significance. In some embodiments the result of such a comparing is used to estimate the relative importance of drug A and substance B to $DO_{diff}$. In some such embodiments the combining involves calculating one or more likelihoods, e.g. a likelihood that $DO_{diff}$ is caused by a factor relating to drug A, a likelihood that $DO_{diff}$ is caused by a factor relating to substance B, a likelihood that $DO_{diff}$ is caused by a factor relating to a known drug A-substance B interaction, and/or a likelihood that $DO_{diff}$ is caused by an unknown factor. Automatic learning techniques may be used to calculate the likelihoods. Calculation of the likelihoods may be iterative, such that the likelihoods are updated as changes are made to parameters relating to drug A and/or substance B, and consequent physiological effects as revealed by the measured values. In some embodiments the output comprises one or more such likelihoods.

It will therefore be appreciated that embodiments of the invention make it possible to determine whether an adverse effect on the patient (as revealed by the measured values) is caused by drug A or by substance B because the effects of drug A and substance B on the subject's physiological characteristics (and therefore the corresponding distribution of the parameters) will be different. A probability that a given effect is due to drug A or substance B can therefore be calculated, e.g. using the methods described above. As will be appreciated, having subject specific information is beneficial, and it can be used to improve the accuracy of this calculation.

In some embodiments the output includes generating a message, e.g. to the subject, which may be shown on a display of the device (if present) and/or emitted by a speaker of the device (if present). In some embodiments the message is transmitted to a remote device 6 associated with the subject and/or a remote device 6 associated with a medical professional. In such embodiments the message may comprise, for example, an SMS, fax or e-mail message. The message may be an alert message. The message may comprise, for example, a warning, a dosing recommendation, or advice to the subject. In some embodiments the message may contain information indicating the level of severity of an interaction between drug A and substance B. In some embodiments the message may indicate a level of urgency (e.g. how soon intervention should be applied). In some embodiments the signal may cause an alarm to be emitted, either by the device or by a remote device with which the device is in communication, e.g. if the output indicates that the subject may be experiencing a severe or life-threatening adverse reaction or side effect. A message to the subject and/or a medical professional is generated in dependence of the output comprising information indicating that an adverse reaction is being experienced by the subject. In other embodiments the output may comprise instructions for an automatic drug administration system. In some embodiments the output may be recorded, e.g. in a database stored on the control unit 3 or the remote server 5, so as to facilitate the recording of the therapeutic drug history of the subject.

The method may further comprise a further step 106, in which a control signal is generated based on the output. For example, if the output comprises a high likelihood that $DO_{diff}$ is caused by a factor relating to drug A, then in preferred embodiments the control signal for a pill dispenser or drug administration system (e.g. an infusion pump) will comprise an instruction to alter one or more parameters relating to the administration of drug A. Preferably in such embodiments the signal comprises an instruction to alter only one parameter, so that the effect of the alteration can be determined using later measurements. If, on the other hand, the output comprises a high likelihood that $DO_{diff}$ is caused by a factor relating to substance B, then in preferred embodiments the signal will comprise an instruction to alter a parameters relating to the administration of substance B. If the output comprises a high likelihood that $DO_{diff}$ is caused by a factor relating to a drug A-substance B interaction, then in some embodiments the signal will comprise a recommendation to reduce or cease the subject's intake of substance B.

In some embodiments a message to the subject as well as a control signal for altering the administration of drug A or substance B may be generated based on the output. In some embodiments, more than one message may be generated, for example a message to the subject and a message to a medical professional may both be generated. It will be appreciated that these messages need not be of the same type.

Thus, the method in FIG. 2 makes use of measurements of a subject's physiological characteristics as well as signatures for all of the substances known to be being taken by the subject, a signature for the physical state which is the desired outcome of the subject's treatment, and optionally, signatures for interactions between substances being taken by the subject, to accurately monitor the effects of the treatment and to quickly detect any adverse reactions and/or drug interactions that may occur. Thus the invention can facilitate timely intervention in a subject's drug therapy to avoid severe adverse reactions and to optimize the beneficial effects.

Figure 3:
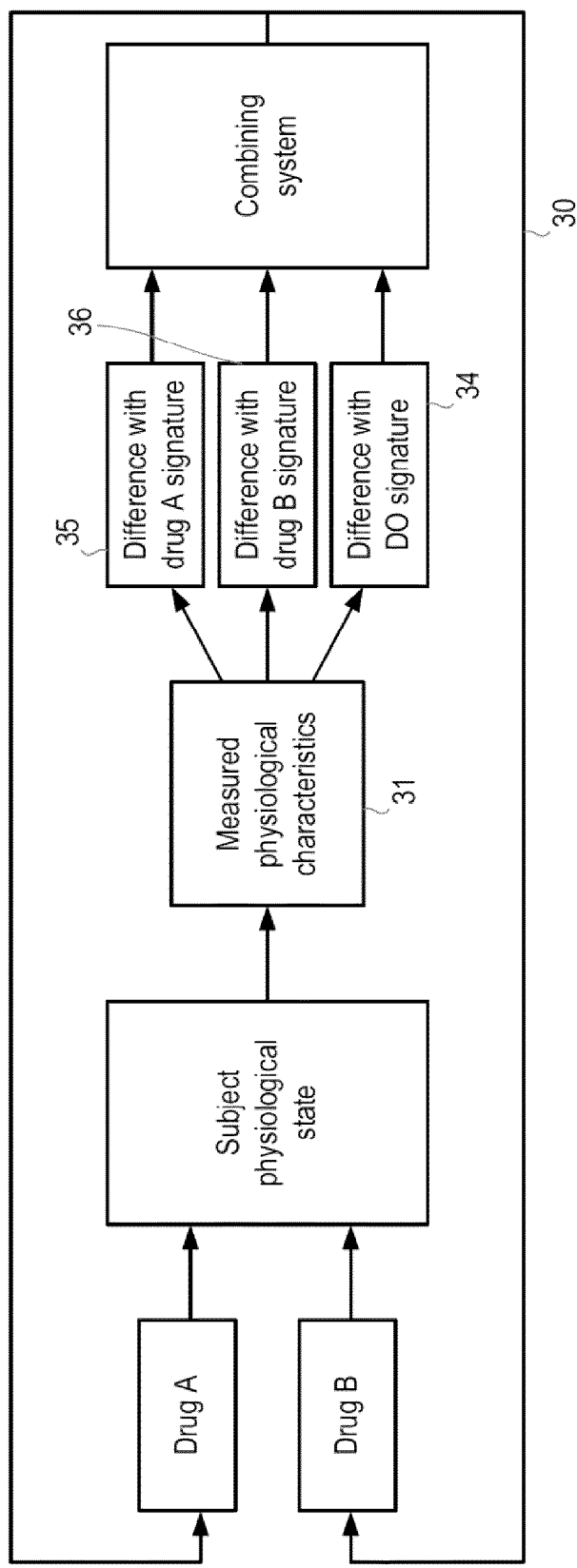
FIG. 3 is a block diagram illustrating the implementation of the method of FIG. 2 according to a specific embodiment of the invention.
Figure 4:
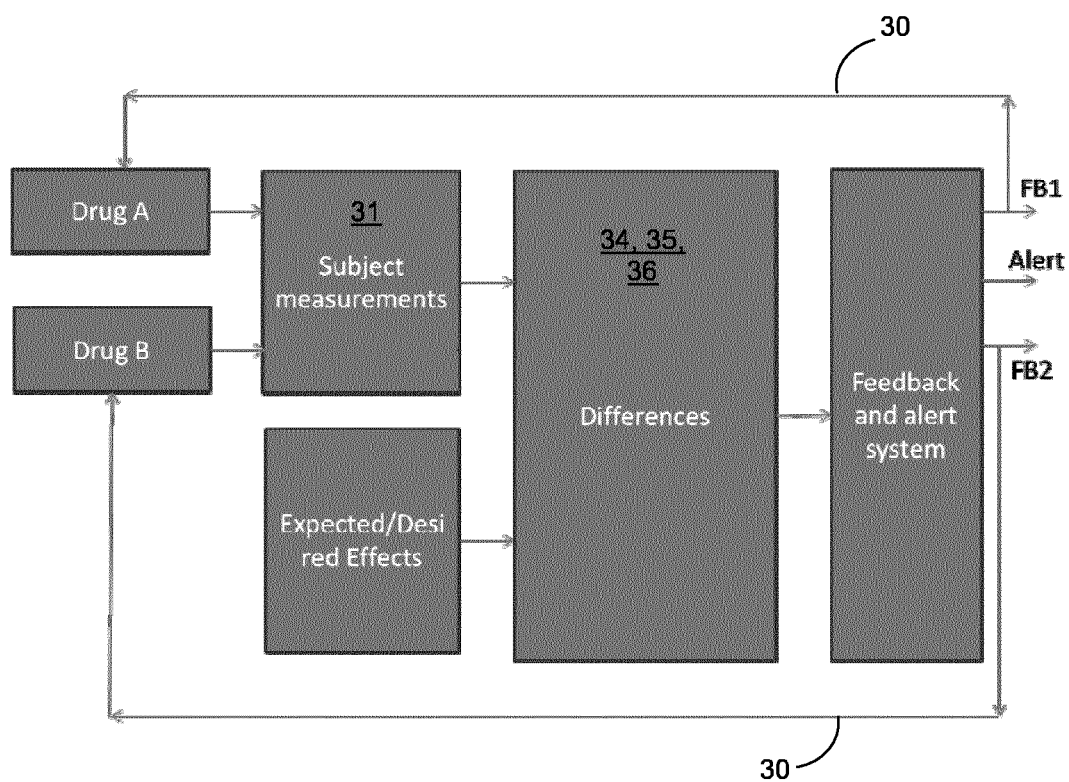
FIG. 4 is a block diagram illustrating the implementation of the method of FIG. 2 according to a specific embodiment of the invention.

FIGS. 3 and 4 illustrate a specific embodiment of the invention in which the invention is used to monitor a subject who is being treated with drug A, but is also known to be simultaneously using a second drug, drug B. In this embodiment the control unit of the device is arranged to determine what changes, if any, may be required to the parameters of the administration of drug A, and whether the effects of drug A may be being altered by the simultaneous use of drug B. Such parameters may include, for example, the dosage amount, the frequency of intake, the form factor of the drug, etc. The method of FIG. 2 is performed as described above, with the drug-related physiological signature for drug B (the drug B signature) corresponding to the substance B signature. Steps 104 and 106 are performed by a combining system, which produces the output.

It will be appreciated that it is desirable to minimize the difference 34 between the measured values of the subject's physiological characteristics 31 and the DO signature. When the measured values 31 substantially match the DO signature, then the treatment has been successful and no (further) adjustments to the administration of drug A and/or drug B are required. However; during the course of a drug treatment, and particularly in the early stages, the measured values 31 can differ from the DO signature, for example because of adverse reactions, interactions between the drugs being administered, interactions between the drugs being administered and other substances (which may be other drugs or foods), or because parameters (such as dosage levels, etc.) of the administration of one or both drugs are sub-optimal. But when, as in the example illustrated by FIG. 3, two drugs are being administered it must be determined which drug is causing the negative effects before it can be determined how the treatment needs to be altered.

This can be achieved by comparing the measured values 31 with the drug A signature and with the drug B signature. In the current example the subject has previously taken drug A in isolation and measured values of their physiological characteristics over the course of this treatment were recorded, so the drug A signature is subject-specific (i.e. it is based on the previously recorded measured values). The subject has not previously taken drug B in isolation, so the drug B signature is not subject-specific. The calculated difference measure 35 between the measured values and the drug A signature is are combined with the calculated difference measure 36 between the measured values and the drug B signature and with the calculated difference measure 34 between the measured values and the DO signature (i.e. step 105 is performed) using the combining system 1 to produce the output.

If the output comprises a high likelihood that the difference measure 34 is caused by factors relating to the administration of drug A, then an output signal 30 containing information relating to the adjustment of one or more of the parameters of the administration of drug A is generated. In the illustrated example, the information contained in the output signal 30 is then used to adjust the intake regimen for drug A. If, on the other hand, the output comprises a high likelihood that the difference measure 34 is caused by factors relating to the administration of drug B, then the output signal 30 will contain information relating to the adjustment of one or more of the parameters of the administration of drug B. If the output comprises a high likelihood that the difference measure 34 is caused by an interaction between drug A and drug B, then the combining unit will decide to alter either a parameter of the administration of drug A or a parameter of the administration of drug B, depending on factors relating to drug A and/or drug B and/or the subject's medical history. The output signal 30 will be generated in accordance with this decision.

Alternatively or additionally to the information relating to the adjustment of one or more drug administration parameters, the output signal may contain information about adverse reactions, side effects, drug-drug interactions and/or drug-food interactions which are potentially occurring. The adjustment of the drug A and/or drug B administration parameters may be performed manually, e.g. by a healthcare professional altering the subject's prescription. In some alternative embodiments the subject is connected to a system which automatically administers drugs A and B, in which case the output signals may comprise direct instructions to the system to alter a parameter of the administration of drug A or drug B. An alert may be issued in addition to the drug administration feedback information, as shown by FIG. 4.

It will be appreciated that the device and method of FIGS. 3 and 4 can be extended to the case where, as well as taking two different drugs, the subject is regularly consuming a food (food C) which has a known physiological effect (as represented by the food C signature). In a further specific embodiment (not illustrated) a measure of the difference between the measured values 31 and the food C signature (this difference measure represents how the effects of food C are altered by the presence of drugs A and B) is calculated and combined together with the difference measures 34, 35 and 36. In this embodiment the output signal 30 can contain information relating to the adjustment of one or more of the parameters of the subject's intake of food C, e.g. if the output comprises a high likelihood that the difference measure 34 is caused by factors relating to the administration of food C.

It will be appreciated that the device and method of the invention can be extended in a similar manner to deal with cases where additional foods and/or drugs are also being taken by the subject.

It should be noted that alternative configurations are possible. For example, in some alternative embodiments, the sensors 2 are used in conjunction with traditional pharmacological monitoring approaches, e.g., therapeutic drug monitoring using immunoassays targeting specific prescription drugs or biomolecules. Such embodiments are useful for improving a diagnosis, for monitoring a subject for other medical purposes, or for detecting medication dosing errors.

There is therefore provided a method and device that allow a subject to be monitored during treatment with a drug so as to monitor the effects of the treatment and detect the occurrence of side effects, adverse reactions, drug-food interactions and/or drug-drug interactions.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method for use in detecting and monitoring effects experienced by a subject taking a first drug, drug A, and at least one other substance, substance B, the method comprising:
   (a) obtaining a plurality of measured values of a physiological characteristic of the subject over a time period after the subject has taken the drug A and the substance B;
   (b) comparing the plurality of measured values to a first predefined signature, a drug A signature, associated with the first drug, that represents an effect that the drug A is expected to have on the physiological characteristic of the subject, and thereby calculating a first measure, $A_{diff}$, of a difference between the plurality of measured values and the drug A signature, wherein $A_{diff}$ represents how the effect of the drug A is altered by a presence of the substance B;
   (c) comparing the plurality of measured values to a second predefined signature, a substance B signature, associated with the at least one other substance, that represents an effect that the substance B is expected to have on the physiological characteristic of the subject and thereby calculating a second measure, $B_{diff}$, of a difference between the plurality of measured values and the substance B signature wherein $B_{diff}$ represents how the effect of the substance B is altered by the presence of the drug A;
   (d) comparing the plurality of measured values to a third predefined signature, a desired outcome (DO) signature, associated with a time variant set of expected values for a desired physiological state of the subject, and thereby calculating a third measure, $DO_{diff}$, of a difference between the plurality of measured values and the DO signature; and
   (e) combining $A_{diff}$ and $B_{diff}$ and $DO_{diff}$ to produce an output, wherein a message to the subject and/or a medical professional is generated in dependence of the output comprising information indicating that an adverse reaction is being experienced by the subject.

2. The method of claim 1, wherein:
the drug A signature comprises expected values for the physiological characteristic after drug A is taken in isolation;
the substance B signature comprises expected values for the physiological characteristic after substance B is taken in isolation; and
the DO signature, comprises values for the physiological characteristic which would be expected after a treatment being administered to the subject is successful.

3. The method of claim 1, further comprising:
comparing the plurality of measured values to a fourth predefined signature, an A-B interaction signature, associated with an interaction between the drug A and the substance B, that represents an effect that the interaction of the drug A and the substance B is expected to have on the physiological characteristic of the subject and thereby calculating a fourth measure, $A\text{-}B_{diff}$, of a difference between the plurality of measured values and the A-B interaction signature, wherein step (e) further comprises:
combining $A_{diff}$ and $B_{diff}$ and $A\text{-}B_{diff}$ and $DO_{diff}$ to produce the output.

4. The method of claim 1, further comprising:
determining, for one or more of the first measure, $A_{diff}$, the second measure, $B_{diff}$, and the third measure $DO_{diff}$, whether the one or more measures exceed(s) a predefined threshold.

5. The method of claim 1, wherein the subject is additionally taking a further substance, substance C, further comprising:
comparing the plurality of measured values to a fifth predefined signature, a substance C signature, associated with the further substance, that represents an effect that the substance C is expected to have on the physiological characteristic of the subject, and thereby calculating a fifth measure, $C_{diff}$, of a difference between the plurality of measured values and the substance C signature, wherein $C_{diff}$ represents how the effect of the substance C is altered by the presence of the drug A and the substance B, wherein step (e) further comprises:
combining $A_{diff}$ and $B_{diff}$ and $C_{diff}$ and $DO_{diff}$ to produce the output.

6. The method of claim 1, wherein one or more of the first measure, $A_{diff}$, the second measure, $B_{diff}$, and the third measure, $DO_{diff}$, comprises a plurality of difference values, wherein each difference value in the plurality of difference values is associated with either a single physiological characteristic or a set of physiological characteristics.

7. The method of claim 6, wherein step (e) further comprises:
assigning a weight to each of the difference values in the plurality of difference values based on one or more of: how relevant the physiological characteristic(s) associated with a given difference value is to a medical history of the subject, how relevant the physiological characteristic(s) associated with a given difference value is to expected effects of the drug A and/or the substance B, a quality of the measured values of the physiological characteristic(s) associated with a given difference value, a variability of the measured values of the physiological characteristic(s) associated with the given difference value.

8. The method of claim 1, wherein the substance B comprises a drug or a food.

9. A drug administration device system comprising a device for use in detecting and monitoring effects experienced by a subject taking a first drug, drug A, and at least one other substance, substance B, the device comprising:
a memory configured to store a first predefined signature, a drug A signature, associated with the first drug, that represents an effect that the drug A is expected to have on a physiological characteristic of the subject, a second predefined signature, a substance B signature, associated with the at least one other substance, that represents an effect that the substance B is expected to have on the physiological characteristic of the subject, and a third predefined signature, a desired outcome (DO) signature, associated with a time variant set of expected values for a desired physiological state of the subject; and
a control unit in communication with the memory, wherein the control unit is configured to:
(i) receive from a sensor a plurality of measured values of one or more physiological characteristics of the subject after the subject has taken the drug A and the substance B;
(ii) compare the received plurality of measured values to the drug A signature and thereby calculate a measure, $A_{diff}$, of a difference between the plurality of measured values and the drug A signature, wherein $A_{diff}$ represents how the effect of the drug A is altered by a presence of the substance B;
(iii) compare the received plurality of measured values to the substance B signature and thereby calculate a measure, $B_{diff}$, of a difference between the plurality of measured values and the substance B signature, wherein $B_{diff}$ represents how the effect of the substance B is altered by a presence of the drug A;
(iv) compare the received plurality of measured values to the DO, signature and thereby calculate a measure, $DO_{diff}$, of a difference between the plurality of measured values and the DO signature;
(v) combine $A_{diff}$ and $B_{diff}$ and $DO_{diff}$ to produce an output;
wherein the drug administration system is configured to alter a parameter of an administration of the drug A and/or the substance B in dependence of the output.

10. A medical instrument or system configured to detect a physiological parameter of a subject and controlling an alarm comprising a device for use in detecting and monitoring effects experienced by a subject taking a first drug, drug A, and at least one other substance, substance B, the device comprising:
a memory configured to store a first predefined signature, a drug A signature, associated with the first drug, that represents an effect that the drug A is expected to have on a physiological characteristic of the subject, a second predefined signature, a substance B signature, associated with the at least one other substance, that represents an effect that the substance B is expected to have on the physiological characteristic of the subject, and a third predefined signature, a desired outcome (DO) signature, associated with a time variant set of expected values for a desired physiological state of the subject; and
a control unit in communication with the memory, wherein the control unit is configured to:
(i) receive from a sensor a plurality of measured values of one or more physiological characteristics of the subject after the subject has taken the drug A and the substance B;
(ii) compare the received plurality of measured values to the drug A signature and thereby calculate a measure, $A_{diff}$, of a difference between the plurality of measured values and the drug A signature, wherein $A_{diff}$ represents how the effect of the drug A is altered by a presence of the substance B;

(iii) compare the received plurality of measured values to the substance B signature and thereby calculate a measure, $B_{diff}$, of a difference between the plurality of measured values and the substance B signature, wherein $B_{diff}$ in represents how the effect of the substance B is altered by a presence of the drug A;

(iv) compare the received plurality of measured values to the DO, signature and thereby calculate a measure, $DO_{diff}$, of a difference between the plurality of measured values and the DO signature;

(v) combine $A_{diff}$ and $B_{diff}$ and $DO_{diff}$ to produce an output; the alarm being in dependence of the output.

* * * * *